US00PP37137P2

(12) United States Plant Patent
Layt

(10) Patent No.: US PP37,137 P2
(45) Date of Patent: Dec. 9, 2025

(54) ***LOMANDRA* PLANT NAMED 'LM380'**

(50) Latin Name: *Lomandra fluviatilis*
Varietal Denomination: LM380

(71) Applicant: Todd Anthony Layt, Richmond (AU)

(72) Inventor: Todd Anthony Layt, Richmond (AU)

( * ) Notice: Subject to any disclaimer, the term of this patent is extended or adjusted under 35 U.S.C. 154(b) by 0 days.

(21) Appl. No.: 18/831,487

(22) Filed: Feb. 21, 2025

(51) Int. Cl.
*A01H 6/12* (2018.01)
*A01H 5/02* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/02
See application file for complete search history.

*Primary Examiner* — Keith O. Robinson
(74) *Attorney, Agent, or Firm* — Samuel R McCoy, Jr.

(57) ABSTRACT

'LM380' is a distinctive *Lomandra fluviatilis* plant which is characterized by a compact arched to weeping habit, a tussock of green to yellow-green foliage, strongly glaucous foliage which give the leaves a dark blue-green to greyed-green general coloration, improved resistance to root and crown rot disease, as well as the uniformity and stability of these characteristics from generation to generation.

2 Drawing Sheets

Latin name of the genus and species: The Latin name of the genus and species of the novel variety disclosed herein is *Lomandra fluviatilis.*

Variety denomination: The inventive variety of *Lomandra fluviatilis* disclosed herein has been given the variety denomination 'LM380'.

BACKGROUND OF THE INVENTION

Parentage: 'LM380' is a seedling selection resulting from an open-pollination and seedling selection process carried out by the inventor at his commercial breeding facility in Clarendon, NSW, Australia. In early spring of 2015, an unnamed female *Lomandra fluviatilis* plant (unpatented) with moderate resistance to crown and root rot disease was grown in close proximity to a plurality of unnamed *Lomandra fluviatilis* male plants (unpatented). These plants were allowed to openly pollinate. The exact pollen parent is unknown, though the population of male plants exhibited a homogenous phenotype that typifies the species. In early summer of 2015, seed was collected from the female plant. In spring of 2016, said seed was germinated and the resulting seedlings were grown to maturity to observe for traits deemed desirable to commercial production and sales. After two years of observation, several progeny were selected for their combination of strong plant vigor and foliage with a bluish hue, and were subsequently planted in the ground to assess their resistance to crown and root rotting diseases. In the fall of 2019, one of these plants was selected for its compact size, blue-green to greyed-green foliage, and improved disease resistance when compared to the female parent and all other progeny.

Asexual Reproduction: 'LM380' was first asexually propagated in 2019 by division of the plant's crown in Clarendon, NSW, Australia and has since been asexually reproduced by meristematic tissue culture propagation. The distinctive characteristics of the inventive 'LM380' variety have proven to be stable through five generations and clones so produced maintain the distinguishing characteristics of the original plant.

SUMMARY OF THE INVENTION

The cultivar 'LM380' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LM380'. These characteristics in combination distinguish 'LM380' as a new and distinct *Lomandra* cultivar:

1. *Lomandra* 'LM380' exhibits a compact, tussock growth habit with arched to weeping foliage; and
2. *Lomandra* 'LM380' exhibits green to yellow-green foliage that is covered with a layer of epicuticular wax which gives the foliage a dark blue-green to greyed-green appearance; and
3. *Lomandra* 'LM380' exhibits improved resistance to *Phytophthora* crown and root rot disease.

BOTANICAL DESCRIPTION OF THE PLANT

Figure 1:
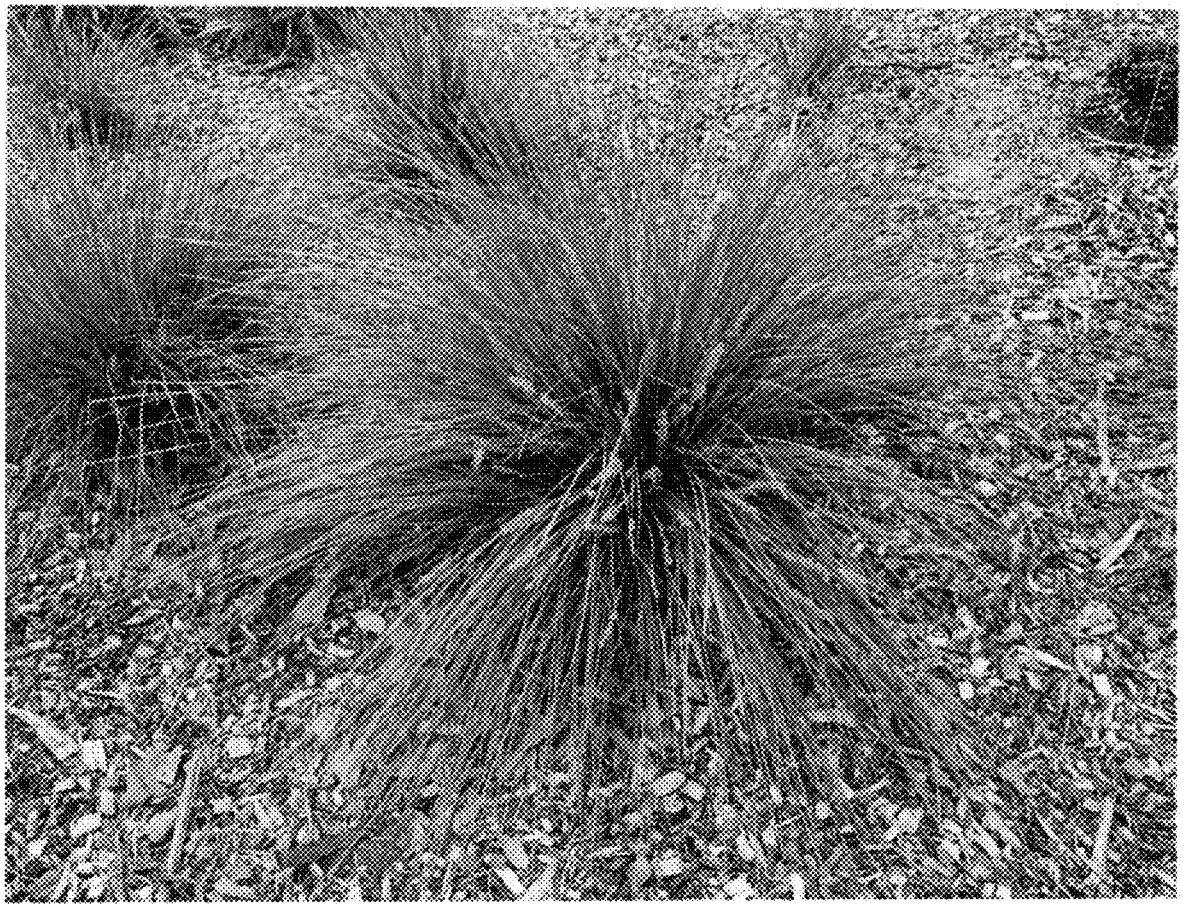
FIG. 1 illustrates, as true as is reasonably possible to obtain in color photographs of this type, an exemplary 'LM380' specimen of approximately 24 months of age in a 250 mm nursery pot, grown at a commercial plant nursery facility in Greeleyville, South Carolina, United States of America.
Figure 2:
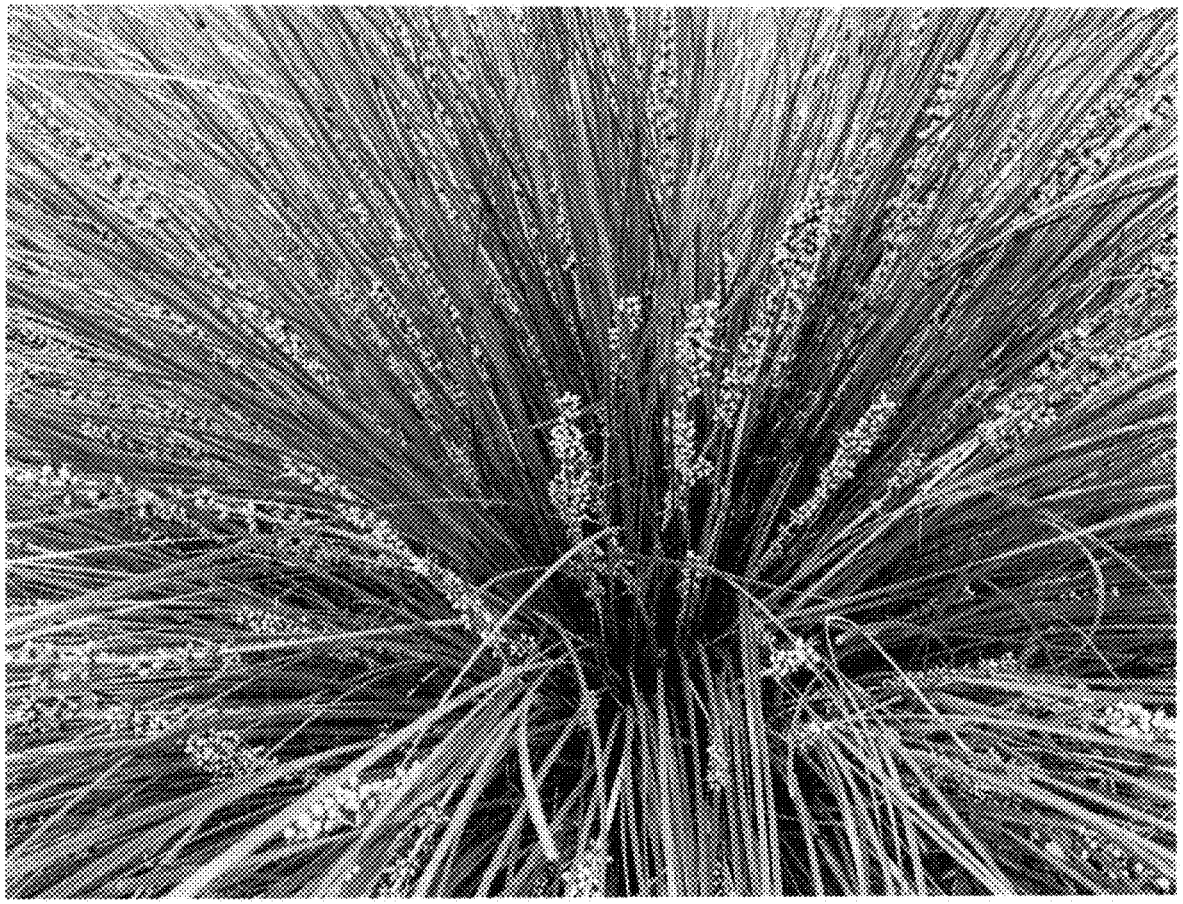
FIG. 2 illustrates, as true as is reasonably possible to obtain in color photographs of this type, the claimed plant's mature foliage and inflorescence of 'LM380' at approximately 24 months of age.

The following is a detailed botanical description of a new and distinct variety of a *Lomandra* ornamental plant known as 'LM380'. Plant observations were made on plants grown in Greeleyville, South Carolina, United States of America. Unless indicated otherwise, the descriptions disclosed herein are based upon observations made in October 2024 of 24-month-old 'LM380' plants grown outdoors, under natural shade, from rooted cuttings in 250 mm nursery pots filled with soilless potting media, maintained with granular slow-release fertilizer, and regularly watered with overhead irrigation. No pest and disease measures were taken.

Those skilled in the art will appreciate that certain characteristics will vary with older or, conversely, younger plants. 'LM380' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition.

A botanical description of 'LM380' and comparisons with the seed parent and most similar variety of common knowledge are provided below.

General plant description:

*Plant habit*.—Grass-like perennial with arched to weeping foliage; rhizomatous plant forming a dense tussock.

*Reproduction*.—Dioecious; male of the species.

*Height*.—Approximately 50 cm at maturity.

*Width*.—Approximately 50 cm at maturity.

*Bloom period*.—Spring.

*Propagation*.—Propagation is accomplished by dividing the crown of the plant and also by way of meristematic tissue culture propagation.

*Crop time*.—Time to initiate rooting is approximately 2 to 3 weeks, depending on the time of year; time to develop a rooted cutting is approximately 12 weeks in a climate-controlled greenhouse. An average crop time in USDA Hardiness Zone 9 is approximately 6 to 9 months to produce a mature and marketable 1-gallon nursery container, beginning with a rooted cutting.

*Environmental tolerances*.—Evergreen in USDA Hardiness Zones 9 through 13 and potentially root hardy in USDA Zone 7; adapt to temperatures ranging from approximately −5 degrees Celsius to 45 degrees Celsius. Shade, drought, and flooding tolerance once established.

*Pest and disease susceptibility or resistance*.—Improved resistance to *Phytophthora* sp. crown and root rot disease.

Roots: Densely rooting; roots are fibrous and distributed evenly throughout the soil profile, from shallow to deep.

Rhizomes: Short, 2 to 3 cm; rhizome color with the leaf sheath removed is white, nearest to RHS 155D; surface texture of the rhizome is smooth.

Foliage:

*Type*.—Evergreen.

*Shape*.—Linear; grass-like.

*Division*.—Simple.

*Arrangement*.—Whorled around an indistinguishable culm.

*Aspect*.—Arched to weeping.

*Apex*.—Tridentate. The leaf apex may become locally necrotic in response to moisture stress.

*Base*.—Sheathed attachment to the culm.

*Margins*.—Entire.

*Texture, adaxial surface*.—Glabrous; smooth; with medium glaucescence.

*Texture, abaxial surface*.—Glabrous; smooth; with medium glaucescence.

*Mature leaf dimensions*.—3 mm wide and 240 mm long, on average. The leaf is generally a uniform width, narrowing only slightly from base to apex.

*Juvenile foliage color, adaxial surface*.—Green, nearest to a mixture of RHS 136C and 139C, generally appearing as green with a blue-green to greyed-green coloration, particularly in direct sunlight due to the epicuticular wax present on the leaf, nearest to a blend of RHS 119A and 189A. With the epicuticular wax covering removed, the leaf surface is a mixture of green and yellow-green, nearest to RHS 143B, 143C, and 144B.

*Juvenile foliage color, abaxial surface*.—Green, nearest to a mixture of RHS 136C and 139C, generally appearing as green with a blue-green to greyed-green coloration, particularly in direct sunlight due to the epicuticular wax present on the leaf, nearest to a blend of RHS 119A and 189A. With the epicuticular wax covering removed, the leaf surface is a mixture of green and yellow-green, nearest to RHS 143B, 143C, and 144B.

*Mature foliage color, adaxial surface*.—Green, nearest to a mixture of RHS 136C and 139C, generally appearing as green with a blue-green to greyed-green coloration, particularly in direct sunlight due to the epicuticular wax present on the leaf, nearest to a blend of RHS 119A and 189A. With the epicuticular wax covering removed, the leaf surface is a mixture of green and yellow-green, nearest to RHS 141A, 143A, and 143B.

*Mature foliage color, abaxial surface*.—Green, nearest to a mixture of RHS 136C and 139C, generally appearing as green with a blue-green to greyed-green coloration, particularly in direct sunlight due to the epicuticular wax present on the leaf, nearest to a blend of RHS 119A and 189A. With the epicuticular wax covering removed, the leaf surface is a mixture of green and yellow-green, nearest to RHS 141A, 143A, and 143B.

*Venation*.—Parallel.

*Vein color, adaxial surfaces*.—Indistinguishable from surrounding foliage.

*Vein color, abaxial surfaces*.—Indistinguishable from surrounding foliage.

Inflorescence:

*Type*.—Racemes containing small clusters of male flowers; some flowers are sessile to the rachis while others are borne on pedicels of varying length.

*Natural flowering season*.—Heavy blooming in spring; sporadic in summer and fall.

*Position*.—Racemes positioned approximately halfway to the foliar plane.

*Overall dimensions*.—16 cm on average in length, including the peduncle and rachis.

*Quantity*.—Very floriferous; inflorescences may potentially arise from every shoot.

*Peduncle*.—Dimensions — Up to 120 mm long and 2 mm in diameter. Attitude — Erect to semi-erect. Strength — Strong. Texture — Smooth. Color — Yellow-green, nearest to RHS 144B.

*Pedicels*.—Dimensions — Up to 10 mm long and 1.25 mm in diameter. Strength — Strong. Texture — Smooth. Color — Yellow-green, nearest to RHS 145A.

Bud:

*Dimensions*.—Approximately 2 mm long and 2 mm wide.

*Bud shape*.—Globose.

*Bud color*.—Yellow, nearest to RHS 10B.

*Rate of bud opening*.—Slow.

Flower:

*Shape*.—Cupuliform; cup-shaped.

*Persistence*.—Non-persistent.

*Aspect*.—Erect.

*Fragrance*.—Non-fragrant.

*Perianth*.—Calyx — Shape — Ovate. Dimensions — Approximately 1 mm in diameter. Color — Yellow, nearest to RHS 10B. Texture — Smooth. Sepals — Arrangement — Alternate. Quantity — Three. Margin — Entire. Apex — Aristate. Base — Obtuse. Texture — Smooth. Sepal color, immature, upper surface — Greyed-orange, nearest to RHS 165D. Sepal color, immature, under surface — Greyed-orange, nearest to RHS 165D. Sepal color, mature, upper surface — Greyed-orange, nearest to RHS 165D. Sepal color, mature, under surface — Greyed-orange, nearest to RHS 165D. Corolla — Arrangement — Alternate; petals unfused. Dimensions — Approximately 2 mm in diameter and 4 mm deep. Petals — Quantity — Three. Arrangement — Alternate. Dimensions — Approximately 1.5 mm long and 1.0 mm wide. Shape — Ovate. Margin — Entire. Apex — Acute. Base — Obtuse. Texture — Smooth. Color when opening, upper side — Yellow-green, nearest to 150D. Color when opening, under side — Yellow-green, nearest to 150D. Color when fully opened, upper side — Yellow, nearest to RHS 10B. Color when fully opened, under side — Yellow, nearest to RHS 10B.

*Bracts*.—Shape — Needle-shaped. Length — range in length from 6 to 9 mm. Apex — Acute. Margin — Entire. Color — Greyed-yellow, nearest to RHS 160D.

Reproduction organs: Not observed.

Seed: Flowers are male; seed is not produced.

COMPARISONS WITH THE PARENT PLANTS

Plants of the new cultivar 'LM380' may be distinguished from the seed parent, and unnamed *Lomandra fluviatilis* plant, by the characteristics described in Table 1, below.

TABLE 1

| Characteristic | 'LM380' | The seed parent. |
|---|---|---|
| Plant size. | Smaller than the seed parent. | Larger than 'LM380'. |
| General coloration of the foliage. | Green with strong dark blue-green to greyed-green suffusion. | Yellow-green with a slight bluish hue. |
| Resistance to *Phytophthora* infection. | More resistant than the seed parent. | Less resistant than 'LM380'. |

While the exact male parentage is unknown, all possible pollen contributors exhibited a homogenous phenotype that is typical of the species. The new cultivar 'LM380' may be distinguished from the species by the characteristics described in Table 2, below.

TABLE 2

| Characteristic | 'LM380' | *Lomandra fluviatilis* |
|---|---|---|
| Plant size. | Smaller than the species. | Larger than 'LM380'. |
| Plant vigor. | More vigorous than the species. | Less vigorous than 'LM380'. |
| General coloration of the foliage. | Green with strong dark blue-green to greyed-green suffusion. | Yellow-green with a slight bluish hue. |
| Resistance to *Phytophthora* infection. | Much more resistant than the species. | Far less resistant than 'LM380'. |

COMPARISON WITH THE MOST SIMILAR VARIETY KNOWN TO THE INVENTOR

The new cultivar 'LM380' may be distinguished from the most similar variety known to the inventor, *Lomandra fluviatilis* 'AU807' (U.S. Plant Pat. No. 23,950), by the characteristics described in Table 3, below.

TABLE 3

| Characteristic | 'LM380' | 'AU807' |
|---|---|---|
| Plant size. | Larger than 'AU807'. | Smaller than 'LM380'. |
| Plant vigor. | More vigorous than 'AU807'. | Less vigorous than 'LM380'. |
| Peduncle length. | Shorter than 'AU807'. | Longer than 'LM380'. |
| Position of the raceme, relative to the foliage. | Positioned within the foliage. | Racemes are at or beyond the foliar plane. |
| Resistance to *Phytophthora* infection. | Much more resistant 'AU807'. | Far less resistant than 'LM380'. |

That which is claimed is:

1. A new and distinct variety of *Lomandra fluviatilis* named 'LM380', substantially as described and illustrated herein.

* * * * *